(12) United States Patent
Montana et al.

(10) Patent No.: US 6,680,338 B2
(45) Date of Patent: Jan. 20, 2004

(54) HYDROXAMIC AND CARBOXYLIC ACID DERIVATIVES

(75) Inventors: John Gary Montana, Cambridge (GB); Andrew Douglas Baxter, Cambridge (GB); David Alan Owen, Cambridge (GB); Robert John Watson, Cambridge (GB)

(73) Assignee: Darwin Discovery Ltd. (GB)

( * ) Notice: Subject to any disclaimer, the term of this patent is extended or adjusted under 35 U.S.C. 154(b) by 156 days.

(21) Appl. No.: 09/777,522

(22) Filed: Feb. 6, 2001

(65) Prior Publication Data

US 2003/0236416 A1 Dec. 25, 2003

Related U.S. Application Data

(63) Continuation-in-part of application No. 09/244,739, filed on Feb. 5, 1999, now abandoned.

(30) Foreign Application Priority Data

Feb. 6, 1998 (GB) .............................. 9802620
Sep. 8, 1998 (GB) .............................. 9819570

(51) Int. Cl.[7] ...................... A61K 31/351; L07D 309/08
(52) U.S. Cl. ...................... 514/451; 514/336; 514/330; 514/428; 546/282.1; 546/226; 548/566; 549/425
(58) Field of Search .................................. 549/425, 451

(56) References Cited

U.S. PATENT DOCUMENTS 5,932,595 A    8/1999   Bender et al.
6,187,924 B1 * 2/2001   Baxter et al. ............. 544/374

FOREIGN PATENT DOCUMENTS

GB    0780386    6/1997
WO    9635714    11/1996

OTHER PUBLICATIONS

Encyclopedia of Immunology Roitt et al. Academic Press, 1993.*

Jankowski K. et al. (1971) "Sur Les Oxathianne–1, 4–one–2*)" *Bulletin de L'Academie Polonaise Des Sciences* 19(11–12):661–672 **English summary.

Witiak, Donald T. et al. (1972) "*cis*– and *trans*–2–Mercaptocyclobutylamines. Synthesis and Antilipolytic Properties in Vitro" *Journal of Medicinal Chemistry* 15(8):803–808.

* cited by examiner

*Primary Examiner*—Jane Fan
(74) *Attorney, Agent, or Firm*—Saliwanchik, Lloyd & Saliwanchik

(57) ABSTRACT

Compounds having therapeutic utility are of formula (I)

$$B-X-(CH_2)_n-CR^2R^3-CR^4R^5-COY \quad (I)$$

wherein n=0–1;

X is $S(O)_{0-2}$;

Y is $OR^1$ or NHOH;

$R^2$ and $R^4$ are independently H or a group (optionally substituted with $R^{10}$) selected from $C_{1-6}$ alkyl, $C_{2-6}$ alkenyl, aryl, $C_{1-6}$ alkyl-aryl, heteroaryl, $C_{1-6}$ alkyl-heteroaryl, heterocycloalkyl, $C_{1-6}$ alkyl-heterocycloalkyl, cycloalkyl and $C_{1-6}$ alkyl-cycloalkyl; and $R^1$, $R^3$ and $R^5$ are independently H or $C_{1-6}$ alkyl, provided that not more than two of $R^2$, $R^3$, $R^4$ and $R^5$ are H; or any of $CR^2R^3$, $CR^4R^5$ and $CR^2-CR^4$ is a cycloalkyl or heterocycloalkyl ring optionally substituted with $R^{10}$ or a group (optionally substituted with $R^{10}$) selected from $C_{1-6}$ alkyl, aryl, $C_{1-6}$ alkyl-aryl, heteroaryl and $C_{1-6}$ alkyl-heteroaryl;

B is heterocycloalkyl (optionally substituted by $R^6$ or $R^7$) bonded through carbon to X, or $C_{1-6}$ alkyl-heterocycloalkyl (optionally substituted with $R^6$ or $R^7$), or a group (substituted with $R^6$) selected from $C_{1-8}$ alkyl, $C_{2-6}$ alkenyl and $C_{2-6}$ alkynyl;

$R^6$ is $N(R^7)_2$, $OR^7$, $COR^7$, $C(=NOR^9)R^7$, $NR^7R^8$, $S(O)_{0-2}R^9$ or $SO_2N(R^7)_2$;

$R^7$ is H or a group selected from $C_{1-6}$ alkyl, aryl, $C_{1-6}$ alkyl-aryl, heteroaryl, $C_{1-6}$ alkyl-heteroaryl, cycloalkyl, $C_{1-6}$ alkyl-cycloalkyl, heterocycloalkyl and $C_{1-6}$ alkyl-heterocycloalkyl, wherein said group is optionally substituted with $R^9$, $COR^9$, $SO_{0-2}R^9$, $CO_2R^9$, $OR^9$, $CONR^1R^9$, $NR^1R^9$, halogen, CN, $SO_2NR^1R^9$ or $NO_2$, and for each case of $N(R^7)_2$ the $R^7$ groups are the same or different or $N(R^7)_2$ is heterocycloalkyl optionally substituted with $R^9$, $COR^9$, $SO_{0-2}R^9$, $CO_2R^9$, $OR^9$, $CONR^1R^9$, $NR^1R^9$, $NR^1R^9$ halogen, CN, $SO_2NR^1R^9$ or $NO_2$, $R^8$ is $COR^7$, $CON(R^7)_2$, $CO_2R^9$ or $SO_2R^9$;

$R^9$ is $C_{1-6}$ alkyl, aryl, $C_{1-6}$ alkyl-aryl, heteroaryl or $C_{1-6}$ alkyl-heteroaryl; and $R^{10}$ is $OR^7$, $COR^7$, $CO_2R^1$, $CON(R^7)_2$, $NR^7R^8$, $S(O)_{0-2}R^9$, $SO_2N(R^7)_2$, CN, halogen or cycloimidyl (optionally substituted with $R^1$);

and the salts, solvates, hydrates, N-oxides, protected amino, protected carboxy and protected hydroxamic acid derivatives thereof.

10 Claims, No Drawings

HYDROXAMIC AND CARBOXYLIC ACID DERIVATIVES

REFERENCE TO RELATED APPLICATION

This Application is a continuation-in-part of application Ser. No. 09/244,739, filed Feb. 5, 1999 now ABN.

FIELD OF THE INVENTION

This invention relates to hydroxamic and carboxylic acid derivatives, and to their use in medicine.

BACKGROUND TO THE INVENTION

Metalloproteinases, including matrix metalloproteinase (MMP), human fibroblast) collagenase, gelatinase and TNF convertase (TACE), and their modes of action, and also inhibitors thereof and their clinical effects, are described in WO-A-9611209, WO-A-9712902 and WO-A-9719075, the contents of which are incorporated herein by reference. MMP inhibitors may also be useful in the inhibition of other mammalian metalloproteinases such as the adamalysin family (or ADAMs) whose members include TNF convertase (TACE) and ADAM-10, which can cause the release of TNFα from cells, and others, which have been demonstrated to be expressed by human articular cartilage cells and also involved in the destruction of myelin basic protein, a phenomenon associated with multiple sclerosis.

Compounds which have the property of inhibiting the action of metalloproteinases involved in connective tissue breakdown, such as collagenase, stromelysin and gelatinase, have been shown to inhibit the release of TNF both in vitro and in vivo. See Gearing et al (1994), Nature 370:555–557; McGeehan et al (1994), Nature 370:558–561; GB-A-2268934; and WO-A-9320047. Al of these reported inhibitors contain a hydroxamic acid zinc-binding group, as do the imidazole-substituted compounds disclosed in WO-A-9523790. Other compounds that inhibit MMP and/or TNF are described in WO-A-9513289, WO-A-9611209, WO-A-96035687, WO-A-9603571 1, WO-A-96035712 and WO-A-96035714.

WO-A-9834915 (published after the earliest priority date claimed herein) discloses compounds of formula I (below) wherein B is heterocycloalkyl (optionally substituted by $R^6$ or $R^7$) bonded through carbon to X.

WO-A-9839315 (published after the earliest priority date claimed herein) discloses compounds of formula I (below) wherein $R^4$ is H and $R^5$ is unsubstituted $C_{1-6}$ alkyl, and B is $C_{1-8}$ alkyl optionally substituted by $OR^7$.

SUMMARY OF THE INVENTION

The invention encompasses compounds of formula (I), many of which are novel, which are useful inhibitors of matrix metalloproteinases and/or TNFα-mediated diseases, including degenerative diseases and certain cancers.

Compounds according to the invention are of the general type represented by formula (I):

  (I)

wherein n=0–1;

X is $S(O)_{0-2}$;

Y is $OR^1$ or NHOH;

$R^2$ and $R^4$ are independently H or a group (optionally substituted with $R^{10}$) selected from $C_{1-6}$ alkyl, $C_{2-6}$ alkenyl, aryl, $C_{1-6}$ alkyl-aryl, heteroaryl, $C_{1-6}$ alkyl-heteroaryl, heterocycloalkyl, $C_{1-6}$ alkyl-heterocycloalkyl, cycloalkyl and $C_{1-6}$ alkyl-cycloalkyl; and $R^1$, $R^3$ and $R^5$ are independently H or $C_{1-6}$ alkyl;

provided that not more than two of $R^2$, $R^3$, $R^4$ and $R^5$ are H; or any of $CR^2R^3$, $CR^4R^5$ and $CR^2$-$CR^4$ is a cycloalkyl or heterocycloalkyl ring optionally substituted with $R^{10}$ or a group (optionally substituted with $R^{10}$) selected from $C_{1-6}$ alkyl, aryl, $C_{1-6}$ alkyl-aryl, heteroaryl and $C_{1-6}$ alkyl-heteroaryl;

B is heterocycloalkyl (optionally substituted by $R^6$ or $R^7$) bonded through carbon to X, or $C_{1-6}$ alkyl-heterocycloalkyl (optionally substituted with $R^6$ or $R^7$), or a group (substituted with $R^6$) selected from $C_{1-8}$ alkyl, $C_{2-6}$ alkenyl and $C_{2-6}$ alkynyl;

$R^6$ is $N(R^7)_2$, $OR^7$, $COR^7$, $C(=NOR^9)R^7$, $NR^7R^8$, $S(O)_{0-2}R^9$ or $SO_2N(R^7)_2$, $R^7$ is H or a group selected from $C_{1-6}$ alkyl, aryl, $C_{1-6}$ alkyl-aryl, heteroaryl, $C_{1-6}$ alkyl-heteroaryl, cycloalkyl, $C_{1-6}$ alkyl-cycloalkyl, heterocycloalkyl and $C_{1-6}$ alkyl-heterocycloalkyl, wherein said group is optionally substituted with $R^9$, $COR^9$, $SO_{0-2}R^9$, $CO_2R^9$, $OR^9$, $CONR^1R^9$, $NR^1R^9$, halogen, CN, $SO_2NR^1R^9$ or $NO_2$, and for each case of $N(R^7)_2$ the $R^7$ groups are the same or different or $N(R^7)_2$ is heterocycloalkyl optionally substituted with $R^9$, $COR^9$, $SO_{0-2}R^9$, $CO_2R^9$, $OR^9$, $CONR^1R^9$, $NR^1R^9$, halogen, CN, $SO_2NR^1R^9$ or $NO_2$;

$R^8$ is $COR^7$, $CON(^7)_2$, $CO_2R^9$ or $SO_2R^9$;

$R^9$ is $C_{1-6}$ alkyl, aryl, $C_{1-6}$ alkyl-aryl, heteroaryl or $C_{1-6}$ alkyl-heteroaryl; and $R^{10}$ is $OR^7$, $COR^7$, $CO_2R^1$, $CON(R^7)_2$, $NR^7R^8$, $S(O)_{0-2}R^9$, $SO_2N(R^7)_2$, CN, halogen or cycloimidyl (optionally substituted with $R^1$);

and the salts, solvates, hydrates, N-oxides, protected amino, protected carboxy and protected hydroxamic acid derivatives thereof.

Combinations of substituents and/or variables are only permissible if such combinations result in stable compounds.

DESCRIPTION OF THE INVENTION

Certain compounds of the invention are preferred. The following groups and variables are particularly preferred.

One group of compounds of the invention has the formula (I) wherein X, Y, n, $R^2$, $R^3$, $R^4$ and $R^5$ are as defined above and B is optionally substituted $C_{1-8}$ alkyl, $C_{2-6}$ alkenyl or $C_{2-6}$ alkynyl, especially an optionally substituted $C_{1-8}$ alkyl group, in particular ethyl or propyl, especially propyl. Compounds of this type are preferably substituted with $R^6$, especially where $R^6$ is $OR^7$. Particular $R^7$ groups are optionally substituted aryl or heteroaryl, especially, optionally substituted phenyl, pyridyl, furanyl or thiophenyl, especially optionally substituted phenyl. $R^7$ when substituted, is in particular substituted with $R^9$, in particular phenyl, $OR^9$, in particular $OCH_3$, F, Cl, Br, I or CN. Particularly preferred substituents are phenyl, $OCH_3$ or Cl.

Another particular group of compounds of the invention has the formula (I) wherein X, Y, n, $R^2$, $R^3$, $R^4$ and $R^5$ are as defined above and B is an optionally substituted $C_{1-6}$ alkyl-heterocycloalkyl group. Especially preferred are those compounds wherein B the alkyl moiety in β is ethyl or propyl, especially ethyl, and the heterocycloalkyl moiety is optionally substituted azetidinyl, pyrrolidinyl or piperidinyl, especially optionally substituted pyrrolidinyl. Compounds of this type are preferably substituted with $R^7$, especially when $R^7$ is optionally substituted aryl or heteroaryl. Particular $R^7$ groups are optionally substituted phenyl, pyridyl, furanyl or thiophenyl, especially optionally substituted phenyl. $R^7$ when substituted, is in particular substituted with $OR^9$, in particular $OCH_3$, F, Cl, Br, I, $NO_2$ or CN.

A further useful group of compounds has the formula (I) wherein X, Y, n, $R^2$, $R^3$, $R^4$ and $R^5$ are as defined above and B is optionally substituted heterocycloalkyl bonded through carbon to X, in particular optionally substituted azetidinyl, pyrrolidinyl or piperidinyl, especially piperidinyl. Compounds of this type are preferably substituted with $R^7$, especially when $R^7$ is optionally substituted aryl or heteroaryl. Particular $R^7$ groups are optionally substituted phenyl, pyridyl, furanyl or thiophenyl, especially optionally substituted phenyl. $R^7$ when substituted, is in particular substituted with $OR^9$, in particular $OCH_3$, F, Cl, Br, I, $NO_2$ or CN. In compounds of the invention when B is optionally substituted heterocycloalkyl bonded through carbon to X and $CR^4R^5$ is preferably an optionally substituted heterocycloalkyl group, then the $CR^4R^5$ group is a saturated heterocyclic moiety having from two to six carbon atoms and one or more heteroatoms from the group O or S (or oxidised versions thereof) which may be optionally benzofused at any available position.

In general in compounds of the invention the most preferred compounds are those wherein any one or more of the following may apply:

X is $SO_2$;

Y is NHOH; and n is O.

$R^2$ or $R^4$ is preferably optionally substituted $C_{1-6}$ alkyl, $C_{1-6}$ alkyl-heteroaryl, or $C_{1-6}$ alkyl-heterocycloalkyl. In compounds of this type, $R^4$ and $R^5$, or $R^2$ and $R^4$, preferably form an optionally substituted cycloalkyl or heterocycloalkyl group, in particular, a cyclobutyl, cyclopentyl, cyclohexyl, azetidinyl, pyrrolidinyl, tetrahydrofuranyl or piperidinyl group, especially cyclobutyl, cyclopentyl or cyclohexyl. In another preference, the heterocycloalkyl group represented by $R^4$ and $R^5$ together is optionally substituted tetrahydropyranyl.

The compounds of the Examples are particularly preferred.

It will be appreciated that the compounds according to the invention can contain one or more asymmetrically substituted carbon atoms. The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof.

It will further be appreciated that the compounds according to the invention may contain an oxime. This oxime can give rise to geometrical isomers, and in each case the invention is to be understood to extend to all such isomers and mixtures thereof.

As used in this specification, alone or in combination, the term "$C_{1-6}$ alkyl" refers to straight or branched chain alkyl moiety having from one to six carbon atoms, including for example, methyl, ethyl, propyl, isopropyl, butyl, tert-butyl, pentyl, hexyl and the like.

The term "$C_{1-8}$ alkyl" refers to straight or branched chain alkyl moiety having from one to eight carbon atoms, including for example, methyl, ethyl, propyl, isopropyl, butyl, tert-butyl, pentyl, hexyl, octyl and the like.

The term "$C_{2-6}$ alkenyl" refers to a straight or branched chain alkyl moiety having two to six carbon atoms and having in addition one double bond, of either E or Z stereochemistry where applicable. This term would include for example, vinyl, 1-propenyl, 1- and 2-butenyl, 2-methyl-2-propenyl etc.

The term "$C_{2-6}$ alkynyl" refers to a straight or branched chain alkyl moiety having two to six carbon atoms and having in addition one triple bond. This term would include for example, ethynyl, 1-propynyl, 1- and 2-butynyl, 1-methyl-2-butynyl etc.

The term "cycloalkyl" refers to a saturated alicyclic moiety having from three to six carbon atoms and includes for example cyclopropyl, cyclobutyl, cyclopentyl, cyclohexyl and the like.

The term "heterocycloalkyl" refers to a saturated heterocyclic moiety having from two to six carbon atoms and one or more heteroatom from the group N, O, S (or oxidised versions thereof) which may be optionally benzofused at any available position. This includes for example azetidinyl, pyrrolidinyl, tetrahydrofuranyl, tetrahydropyranyl, piperidinyl, benzodioxole and the like.

The term "aryl" refers to an aromatic carbocyclic radical having a single ring or two condensed rings. This term includes, for example, phenyl and naphthyl.

The term "heteroaryl" refers to aromatic ring systems of five to ten atoms of which at least one atom is selected from O, N and S, and includes for example furanyl, thiophenyl, pyridyl, indolyl, quinolyl and the like.

The term "halogen" means fluorine, chlorine, bromine or iodine.

The term "benzofused" refers to the addition of a benzene ring sharing a common bond with the defined ring system.

The term "cycloimidyl" refers to a saturated ring of five to ten atoms containing the atom sequence. —C(=O)NC(=O)—. The ring may be optionally benzofused at any available position. Examples include succinimidoyl, phthalimidoyl and hydantoinyl.

The term "optionally substituted" means optionally susbsituted with one or more of the groups specified, at any available position or positions.

The terms "protected amino", "protected carboxy" and "protected hydroxamic acid" mean amino, carboxy and hydroxamic acid groups which can be protected in a manner familiar to those skilled in the art. For example, an amino group can be protected by a benzyloxycarbonyl, tert-butoxycarbonyl, acetyl or like group, or may be in the form of a phthalimido or like group. A carboxyl group can be protected in the form of a readily-cleavable ester such as the methyl, ethyl, benzyl or tert-butyl ester. A hydroxamic acid may be protected as either N or O-substitued derivatives, such as O-benzyl or O-tert-butyldimethylsilyl.

Salts of compounds of formula (I) include pharmaceutically-acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically-labile ester of formula $CO_2R^{11}$ where $R^{11}$ may be an ethyl, benzyl, phenethyl, phenylpropyl, α- or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trimethylbenzyloxymethyl or pivaloylmethyl group.

Compounds of the general formula (I) may be prepared by any suitable method known in the art and/or by the following processes.

It will be appreciated that, where a particular stereoisomer of formula (I) is required, the synthetic processes described herein may be used with the appropriate homochiral starting material and/or isomers maybe resolved from mixtures using conventional separation techniques (e.g. HPLC).

The compounds according to the invention may be prepared by the following process. In the description and formulae below the groups $R^1$, $R^2$, $R^3$, $R^4$, $R^5$, $R^6$, $R^7$, $R^8$, $R^9$, $R^{10}$, $R^{11}$, B, X and Y are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see Greene et al, "Protective Groups in Organic Synthesis", Wiley Interscience.

A process for preparing compounds of general formula (I) comprises reacting a compound of formula B—SH (II) with (a) an alkylating agent of formula Z—(CH$_2$)$_n$—CR$^3$R$^3$—CR$^4$R$^5$—COY (III) (wherein Z represents a suitable leaving group e.g. a halogen such as bromine, or an alkylsulphonate ester such as methanesulphonate), or (b) (when n=0 and $R^5$=H) an acrylate of formula CR$^2$R$^3$=CR$^4$—COY (IV) or (c) a lactone of the formula (V)

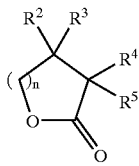

(V)

An alternative process for preparing compounds of formula (I) involves reacting a compound of formula BSQ (XII), where Q is a suitable labile group, such as acetyl, in the presence of a strong base such as hexamethyldisilazide with (a) an alkylating agent of formula (III) or (b) an acrylate of formula (IV).

A further alternative process for preparing compounds of formula (I) involves reacting a compound of formula B—Z (VI) with a compound of formula Q—S—(CH$_2$)$_n$CR$^2$R$^3$CR$^4$R$^5$COY (VII), where Z is defined above and Q is a suitable labile group, such as acetyl, in the presence of a strong base such as hexamethyldisilazide in an inert solvent such as tetrahydrofuran. Compounds of formula (VII) may be prepared by reaction of a compound of formula QSH (VIII) with a compound (III), (IV) or (V) as defined above, optionally in the presence of an organic or inorganic base.

Alkylating agents of formula (III) can be obtained in chiral or racemic form. Many of these derivatives can be readily obtained from commercially available starting materials using methods known to those skilled in the art (e.g. see WO-A-9005719).

Acrylates of formula (IV) may be prepared by the condensation of a carbonyl compound of the form R$^4$CH$_2$COY (IX) with ketones or aldehydes of formula R$^2$COR$^3$ (X). This reaction may be performed under a variety of conditions known to those skilled in the art, for example under the action of a strong base such as lithium diisopropylamide in an inert solvent such as tetrahydrofuran, to give an intermediate alcohol of the form R$^2$C(OH)R$^3$CHR$^4$COY (XI). These alcohols (XI) may or may not be isolated: dehydration may occur in situ or be performed separately under appropriate conditions such as aqueous acid to give the desired acrylate (IV).

Lactones of formula (V) may be prepared by chemistry known to those skilled in the art. For example see EP-A-0780386.

Many compounds of formula (II) and (VIII) are available commercially, or may be prepared from compounds of the form B—Z (VI) by standard methods (for example, see WO-A-9611209).

Many compounds of formula (VIII), (VI), (IX) and (X) are available commercially, or may be prepared from compounds available commercially by standard methods. Other substituents described by $R^2$, $R^4$, or $R^6$ or can be introduced by standard chemical transformations known to those skilled in the art.

Compounds of formula (I) may also be prepared by interconversion of other compounds of formula (I). Thus, for example, a compound of formula (I) wherein $R^2$ is a C$_{1-6}$ alkyl group may be prepared by hydrogenation (using palladium on carbon in suitable solvent, such as an alcohol, e.g. ethanol) of a compound of formula (I) wherein $R^2$ is a C$_{2-6}$ alkenyl group. Further, a compound of formula (I) wherein X is S(O)$_{1-2}$ may be prepared by oxidation of a compound of formula (I) wherein X is S for example, using Oxone®, in a suitable solvent, such as methanol. Compounds of formula (I) wherein B is (CH$_2$)$_{1-8}$OR$^7$ (where R$^7$ is aryl or heteroaryl) may be prepared, for example, by activating a corresponding compound of formula (I), wherein B is (CH$_2$)$_{1-8}$OH, with an appropriate activating agent, such as triphenylphosphine or diethylazodicarboxylate, followed by addition of R$^7$OH, using an inert solvent, such as tetrahydrofuran.

Esters of formula (I) may be converted to carboxylic acids of formula (I) using methods known to those skilled in the art, such as hydrolysis in the presence of an aqueous base, such as lithium hydroxide, in a suitable alcoholic solvent, such as methanol. Carboxylic acids of general formula (I) (Y=OH) may be converted to other compounds of formula (I) such as esters (Y=OR$^1$) or hydroxamic acids (Y=NHOH) using methods known to those skilled in the art, or as described in the Examples, hereinafter.

Compounds of formula (I) may also be prepared by interconversion of other compounds of formula (I). Thus, for example, a compound of formula (I) wherein $R^2$ is a C$_{1-6}$ alkyl group may be prepared by hydrogenation (using palladium on carbon in suitable solvent, such as an alcohol, e.g. ethanol) of a compound of formula (I) wherein $R^2$ is a C$_{2-6}$ alkenyl group. Further, a compound of formula (I) wherein X is S(O)$_{1-2}$ may be prepared by oxidation of a compound of formula (I) wherein X is S.

Carboxylic acids of general formula (I) (Y=OH) may be converted to other compounds of formula (I) such as esters (Y=OR$^1$) or hydroxamic acids (Y=NHOH) using methods known to those skilled in the art.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to the stromelysins, collagenases and gelatinases. Compounds according to the invention may also exhibit in vitro inhibition of membrane shedding events known to be mediated by metalloproteinases, for example, α-APP, ACE, TGF-α, TNF-α, Fas ligand, TNFR-I, TNFR-II, CD30, Il-6R, CD43, CD44, CD 16-I, CD 16-II, Folate receptor, CD23, or IL-1RII.

The activity and selectivity of the compounds may be determined by use of the appropriate enzyme inhibition test, for example as described in Examples A-M of WO-A-9805635, by the assay for the inhibition of CD23 shedding described in PCT/GB98/03395, or by the following assay of TNF RI shedding.

The potency of the compounds of general formula (I) to act as inhibitors of the production of TNF RI is determined using the following procedure. A 100 $\mu$M solution of the inhibitor being tested or dilutions thereof is incubated at 37° C. in an atmosphere of 5% $CO_2$ with peripheral blood mononuclear cells (PBMC). PBMC are isolated from buffy coats by standard procedures using Ficoll. A 100 $\mu$M solution of the inhibitor being tested or dilutions thereof is incubated for 22 hours at 37° C. in an atmosphere of 5% $CO_2$ with $1\times10^6$/ml PBMC stimulated with LPS. The cells are centrifuged down and the supernatant is assayed for TNF RI using a commercially available ELISA kit (R & D Systems). The activity in the presence of 0.1 mM inhibitor or dilutions thereof is compared to activity in a control devoid of inhibitor and results reported as that inhibitor concentration effecting 50% inhibition of the production of TNF RI.

This invention also relates to a method of treatment for patients (including man and/or mammalian animals raised in the dairy, meat or fur industries or as pets) suffering from disorders or diseases which can be attributed to stromelysin as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNF and MMPs. Accordingly in another aspect, this invention concerns:

a method of management (by which is meant treatment of prophylaxis) of disease or conditions mediated by TNF and/or MMPs in mammals, in particular in humans, which method comprises administering to the mammal an effective, amount of a compound of formula (I) above, or a pharmaceutically acceptable salt thereof, and a compound of formula (I) for use in human or veterinary medicine, particularly in the management (by which is meant treatment or prophylaxis) of diseases or conditions mediated by TNF and/or MMPs; and the use of a compound of formula (I) in the preparation of an agent for the management (by which is meant treatment or prophylaxis) of diseases or conditions mediated by TNF and/or MMPs.

The disease or conditions referred to above include inflammatory diseases, autoimmune diseases, cancer, cardiovascular diseases, diseases involving tissue breakdown such as rheumatoid arthritis, osteoarthritis, osteoporosis, neurodegeneration, Alzheimer's disease, stroke, vasculitis, Crohn's disease, ulcerative colitis, multiple sclerosis, periodontitis, gingivitis and those involving tissue breakdown such as bone resorption, haemorrhage, coagulation, acute phase response, cachexia and anorexia, acute infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema, anaphylaxis, restenosis, congestive heart failure, endometriosis, atherosclerosis, endosclerosis and aspirin-independent anti-thrombosis.

Compounds of formula (I) may also be useful in the treatment of pelvic inflammatory disease (PID), age-related macular degeneration and cancer-induced bone resorption. Further, they can be used in the treatment of lung diseases, e.g. selected from cystic fibrosis, adult respiratory distress syndrome (ARDS), emphysema, bronchitis obliterans-organising pneumonia (BOOP), idiopathic pulmonary fibrosis (PIF), diffuse alveolar damage, pulmonary Langerhan's cell granulamatosis,: pulmonary lymphangioleiomyomatosis (LAM) and chronic obstructive pulmonary disease (COPD).

For the treatment of rheumatoid arthritis, osteoarthritis, and in diseases and indications resulting from the over-expression of matrix metalloendoproteinases such as found in certain metastatic tumour cell lines or other diseases mediated by the matrix metalloendoproteinases or increased TNF production, the compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874, to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as absolution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. For the purposes of this specification, topical application includes mouth washes and gargles.

Dosage levels of the order of from about 0.05 mg to about 140 mg per kilogram of body weight per: day are useful in the treatment of the above-indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day).

The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following Examples illustrate the invention. The following abbreviations are used:

RT=Room Temperature THF=Tetrahydrofuran h=Hour
Intermediate 1 2,7-Dioxaspiro[3.5]nonan-1-one Was prepared according to the procedure outlined in EP-A-0780386, as a colourless oil (5.2 g).
Intermediate 2 1-Bromo-3-(4-chlorophenoxy)propane Sodium hydride (3.3 g, 60% dispersion in oil) was added to a solution of 4-chlorophenol (9.0 g) in DMF (30 ml) at 0° C. and the mixture was stirred for 30 min, then 1,3-dibromopropare (22.5 g, 1.5 eq) was added. The mixture was stirred at room temperature for 18 h, then added to water (300 ml) and extracted with ether. The solvent was washed with 5% NaOH and brine, dried over $MgSO_4$ and evaporated and the residue purified on silica gel, eluting with 1:1 ether/hexane, to give the title compound (13.5 g) as a colourless oil.
TLC $R_f$0.73 (ether).
Intermediate 3 1-Acetylsulfanyl-3-(4-chlorophenoxy)propane A solution of Intermediate 2 (6.0 g) in DMF (50 ml) was treated with potassium thioacetate (5.7 g) at room temperature for 3 h, then the brown solution was added to 5% sodium bicarbonate solution and extracted with ether (3×200 ml). The solvent was washed with water (200 ml) and brine, dried over $MgSO_4$ and evaporated to give the title compound (5.50 g) as a beige solid.

TLC $R_f$ 0.54 (ether).

The following compound was prepared in a similar manner:

Intermediate 4 Thioacetic acid S-(3-phenoxypropyl)ester

Prepared in the same manner as Intermediate 3 from 3-phenoxypropyl bromide (8 ml) and potassium thioacetate (7.01 g) to give the title compound (10.35 g) as an orange oil.

TLC $R_f$ 0.74 (1:1 hexane-ethyl acetate)

Intermediate 5 Methyl 4-iodomethyl-tetrahydropyran-4-carboxylate

To a stirred solution of methyl tetrahydropyran-4-carboxylate (3.00 g) in anhydrous THF (50 ml) under nitrogen at 0° C. was added a solution of lithium di-isopropylamide (2.0 M, 10.9 ml). After 30 minutes, diiodomethane (8.36 g) was added and the mixture was allowed to warm up to RT and then stirred for 1 h. The mixture was poured onto water (50 ml) and extracted with ether (3×40 ml). The combined ether layers were washed with water (2×20 ml), aqueous hydrochloric acid (2 M, 20 ml), water (20 ml) and brine (20 ml), dried ($MgSO_4$) and evaporated under reduced pressure. The residue was purified on silica gel, eluting with 3:1 hexane/ether, to give the title compound (3.11 g) as a colourless oil.

TLC $R_f$ 0.26 (3:1 hexane/ether)

The following compound was prepared in a similar manner:

Intermediate 6 Methyl 1-iodomethylcycloheianecarboxylate

Prepared in the same manner as Intermediate 5 from methyl cyclohexane-carboxylate (0.32 ml) and diiodomethane (0.18 ml) to yield the title compound as a pale yellow oil (0.62 g, 97%)

TLC $R_f$ 0.84 (1:1 hexane/diethyl ether)

Intermediate 7 Methyl 4-Acetylsulfanylmethyl-tetrahydropyran-4-carboxylate

A solution of Intermediate 4 (3.05 g) in DMF (20 ml) was treated with potassium thioacetate (1.47 g) at room temperature for 18 h, then the brown solution was added to 5% sodium bicarbonate solution and extacted with ether (3×200 ml). The solvent was washed with water (200 ml) and brine, dried over $MgSO_4$ and evaporated to give the title compound (2.42 g) as a white solid.

TLC $R_f$ 0.44 (1:1 hexane/ether).

Intermediate 8 1-Acetylsulfanylmethyl-cyclobutanecarboxylic acid ethyl ester n-Butyllithium (49.8 ml of a 1.6 N solution in hexanes) was added gradually to a solution of diisopropylamine (11.2 ml) in tetrahydrofuran (90 ml) cooled in an acetone-cardice bath under an atmosphere of nitrogen. After stirring for 30 minutes, ethyl cyclobutanecarboxylate (10 ml) was added. The mixture was stirred for a further 30 minutes before addition of diiodomethane (6.4 ml), and then for 3 hours, during which it warmed to room temperature. It was quenched with water (30 ml) and the tetrahydrofuran. evaporated in vacuo. The residue was partitioned between ethyl acetate (100 ml) and water (100 ml). The aqueous was extracted with ethyl acetate (100 ml). The combined organics were dried ($MgSO_4$) and the solvent removed in vacuo to give a brown oil which was dissolved in N,N-dimethylformamide (40 ml) and added to a suspension of potassium thioacetate (8.3 g) in N,N-dimethylformamide (40 ml) at room temperature. The mixture was stirred for 18 hours before evaporation of the solvent in vacuo. The residue was partitioned between ethyl acetate (100 ml) and water (100 ml). The organics were washed with water (100 ml), dried ($MgSO_4$) and the solvent removed in vacuo to give the title compound (13.5 g) as a brown oil.

TLC $F_f$ 0.59 (2:1 heptane-ethyl acetate)

Intermediate 9[1-(4-Nitro-phenyl)-piperidin-4-yl]-methanol

Lithium aluminium hydride was added gradually to a solution of ethyl 1-4(nitrophenyl)-4-piperidine carboxylate (2.5 g) in THF (30 ml) cooled in an ice bath. The mixture was stirred for 18 h at room temperature before being quenched with water (1 ml), 15% aqueous sodium hydroxide (1 ml) and water (3 ml), filtered and evaporated under reduced pressure. The residue was partitioned between ethyl acetate (30 ml) and water (20 ml) washed with water (20 ml), dried ($MgSO_4$), evaporated and the residue purified by chromatography on silica, eluting with 3% methanol in dichloromethane, to give the title compound (0.95 g) as a yellow solid.

TLC $R_f$ 0.2 (3% methanol in dichloromethane)

Intermediate 10 3-(2-Iodo-ethyl)-1-(4-nitro-phenyl)-pyrrolidine

A mixture of iodine (1.12 g) and triphenylphosphine (1.16 g) in toluene (20 ml) was stirred for 15 minutes before addition of Intermediate 9 (951 mg). The mixture was heated to reflux for 6 hours. After cooling to room temperature, the mixture was partitioned between water (20 ml) and ether (20 ml). The organics were washed with water (4×20 ml), aqueous sodium bicarbonate (20 ml), and brine (15 ml) before being dried (MgSO4) evaporated and the residue purified by chromatography on silica, eluted with 20% ethyl acetate in hexane, to give the title compound (435 mg) as a orange solid.

TLC $R_f$ 0.55 (30% ethyl acetate in hexane)

Intermediate 11 4-Hydroxypiperidine-1-carboxylic acid tert-butyl ester

Di-tert-butyl dicarbonate (20.5 g) was added to an ice-cold solution of 4-hydroxypiperidine (10.0 g) in dichloromethane (150 ml), followed by the dropwise addition of triethylamine (27.5 ml). The reaction was stirred for 1 h in the ice bath and then at room temperature for a further 20 h. The dichloromethane solution was then washed with water (80 ml, then 40 ml), 1.0 M hydrochloric acid (220 ml), water (40 ml), saturated sodium bicarbonate solution (30 ml), dried ($MgSO_4$), and evaporated under reduced pressure to give the title compound as a colouless oil, which crystallised on standing(18.9 g, 100%).

TLC $R_f$ 0.40 (5% methanol/dichloromethane)

Intermediate 12 4-(Acetylsulfanyl)piperidine-1-carboxylic acid tert-butyl ester

Triphenylphosphine (7.37 g) and Intermediate 11 (4.71 g) were dissolved in tetrahydrofuran (40 ml), under a nitrogen atmosphere, and cooled to −78° C. Diethyl azodicarboxylate (4.42 ml) was added via syringe, followed by thiolacetic acid (2.17 ml). The reaction was then stirred for 18 h, slowly warming to room temperature. The reaction was reduced in vacuo and the residue redissolved in ethyl acetate (150 ml) and washed with saturated sodium bicarbonate solution (3×20 ml), water (2×20 ml) and saturated brine (20 ml). The organic phase was then dried ($Na_2SO_4$), and diluted with hexane (150–200 ml). The resultant precipitate was removed by filtration, and the filtrate evaporated under reduced pressure. The pale green residue was then purified by silica gel column chromatography with 1% methanol in dichloromethane as eluent to yield the title compound as a colourless oil (0.99 g, 16%).

TLC $R_f$ 0.23 (1% methanol/dichloromethane)

EXAMPLE 1

4-((3-(4-Chlorophenoxy)propylsulfanyl)methyl)-tetrahydropyran-4-carboxylic Acid A solution of Intermediate 3 (0.80 g) in methanol was treated with a solution of sodium hexamethyldisilazide (1 M in THF, 3.3 ml) at 0° C. and the resulting mixture was stirred for 2 h, then a solution of Intermediate 1 (460 mg) in methanol was added. The mixture was stirred for 18 h, then evaporated and the residue dissolved in water and washed with diethyl ether. The aqueous phase was acidified with citric acid and extracted with dichloromethane; the organic layer was then washed with brine, dried over $MgSO_4$ and evaporated to give the title compound (0.12 g) as a colourless oil.
TLC $R_f$0.54 (ether)

EXAMPLE 2

Methyl 4-(3-Hydroxypropylsulfanylmethyl)tetrahydropyran-4-carboxylate

To a stirred solution of Intermediate 7 (2.50 g) in methanol (100 ml) under nitrogen at 0° C. was added a solution of sodium hexamethyldisilazide (1M in THF, 11.3 ml) and the resulting mixture was stirred for 10 mins, then a solution of 3-bromopropanol (1.5 g) was added. The mixture was stirred for 6 h, then evaporated and the residue treated with water (100 ml) and extracted with dichloromethane (4×50 ml). The combined dichloromethane extracts were washed with water (2×50 ml), brine (50 ml), dried over $MgSO_4$ and evaporated. The residue was purified on silica gel eluting with 2:1 ethyl acetate/hexane, to give the title compound (2.41 g) as a colourless oil. TLC $R_f$0.26 (2:1 ethyl acetate/hexane).

The following compounds were prepared in a similar manner:

EXAMPLE 3

2-(3-Phenoxypropylsulfanyl)cyclopentanecarboxylic acid methyl ester

Prepared in the same manner as Example 2 from Intermediate 4 (199 mg) and methyl 1-cyclopentene-1-carboxylate (0.11 6 ml) to give, after chromatography on silica, eluted with 1:1 hexane-dichloromethane followed by 1:3 hexane-dichloromethane, the title compound (204 mg) as a colourless oil.
TLC $R_f$0.31 (1:1 hexane-ethyl acetate)
MS 295 ($MH^+$)

EXAMPLE 4

1-{2-[1-(4-Nitrophenyl)pyrrolidin-3-yl]ethylsulfanylmethyl}-cyclobutanecarboxylic acid ethyl ester Prepared in the same manner as Example 2 from Intermediate 8 (0.15 g) and Intermediate 10 (0.21 g) to give the title compound (240 mg) as an orange solid.
TLC $R_f$0.47 (30% ethyl acetate in hexane)
MS 393 ($MH^+$)

EXAMPLE 5

Methyl 4-((3-(4-Methoxyphenoxy)propylsulfanyl)methyl)-tetrahydropyran-4-carboxylate To a stirred solution of Example 2 (500 mg) and triphenylphosphine (528 mg) in dry THF (25 ml) at 0° C. under nitrogen, was added diethylazodicarboxylate (351 mg). After 5 min a solution of 4-methoxyphenol (250 mg) in THF was added. The mixture was stirred for 2 h with the temperature rising to RT, then poured into ether (100 ml) and washed with water (2×25 ml), sodium hydroxide solution (1M; 25 ml), brine (25 ml) and dried over $MgSO_4$. Evaporation and purification on silica gel eluting with 2:1 hexane/ethyl acetate, gave the title compound (415 mg) as a colourless oil.
TLC $R_F$0.25 (2:1 hexane/ethyl acetate).
Similarly prepared were:

EXAMPLE 6

Methyl 4-((3-(4-Phenylphenoxy)propylsulfanyl)methyl)-tetrahydropyran-4-carboxylate From Example 2(500 mg) and 4-phenylphenol (343 mg) as a white solid (298 mg).
TLC $R_f$0.45 (2:1 hexane/ethyl acetate).

EXAMPLE 7

Methyl 4-((3-(3-Pyridyloxy)propylsulfanyl)methyl)-tetrahydropyran-4-carboxylate From Example 2(500 mg) and 3-hydroxypyridine (191 mg) as a colourless oil (360 mg).
TLC $R_f$0.19 (2:1 ethyl acetate/hexane).

EXAMPLE 8

Methyl 4-((3-(4-Methoxyphenoxy)propylsulfonyl)methyl)-tetrahydropyran-4-carboxylate To a stirred solution of Example 5 (400 mg) in methanol (10 ml) at RT was added a solution of Oxone (1.04 g) in water (20 ml). Stirring was continued for 18 h before diluting with water (50 ml) and extracting with dichloromethane (4×25 ml). The combined organic layers were washed with water (25 ml), brine (25 ml), dried over $MgSO_4$ and evaporated to give the title compound (385 mg) as a colourless oil.
TLC $R_f$0.33 (2:1 ethyl acetate/hexane).
Similarly prepared were:

EXAMPLE 9

Methyl 4-((3-(4-Phenylphenoxy)propylsulfonyl)methyl)-tetrahydropyran-4-carboxylate From Example 6 (290 mg) as a white solid (303 mg).
TLC $R_f$0.33 (2:1 ethyl acetate/hexane).

EXAMPLE 10

Methyl 4-((3-(3-Pyridyloxy)propylsulfonyl)methyl)-tetrahydropyran-4-carboxylate From Example 7 (325 mg) as a colourless oil (350 mg).
TLC $R_f$0.15 (ethyl acetate).

EXAMPLE 11

1-{2-[1-(4-Nitrophenyl)pyrrolidin-3-yl]-ethanesulfonylmethyl}-cyclobutanecarboxylic acid ethyl ester Prepared in the same manner as Example 8 from Example 4 (0.24 g) and oxone (0. 56 g) to give, after chromatography on silica eluted with 2:1 hexane-ethyl acetate, the title compound (60 mg) as a white solid.

TLC $R_f$ 0.29 (1:1 hexane-ethyl acetate)
MS 425 (MH$^+$)

EXAMPLE 12

2-(3-Phenoxypropane-1-sulfonyl)
cyclopentanecarboxylic acid methyl ester

Prepared in the same manner as Example 8 from Example 3 (202 mg) and oxone (613 mg) to give, after chromatography on silica, eluted with 30% hexane in ether, the title compound (163 mg) as a colourless gum.
TLC $R_f$ 0.49 (30% hexane in ether)
MS 327 (MH$^+$)

EXAMPLE 13

4-((3-(4-Chlorophenoxy)propylsulfonyl)methyl)
-tetrahydropyran-4-carboxylic Acid Oxone (0.42 g) was added to a solution of Example 1 (0.12 g) in methanol (10 ml) and water (5 ml) at room temperature and the mixture was stirred for 3 h. The mixture was then evaporated to half volume, diluted with water (5 ml) and extracted with dichloromethane (2×20 ml). The organic layer was then washed with brine, dried over MgSO$_4$ and evaporated and the residue purified by flash column chromatography on silica gel, eluting with ethyl acetate/acetic acid (99:1) to give the title compound (70 mg) as a white solid.
TLC $R_f$ 0.70
MS 376 (M$^+$)

EXAMPLE 14

4-((3-(4-Methoxyphenoxy)propylsulfonyl)methyl)
-tetrahydropyran-4-carboxylic Acid To a stirred solution of Example 8 (380 mg) in methanol (30 ml) was added a solution of lithium hydroxide (206 mg) in water (10 ml). The mixture was refluxed for 1.5 h, cooled to RT and diluted with water (50 ml). The aqueous mixture was washed with ether (2×20 ml), acidified (2M HCl, pH1) and extracted with ethyl acetate (5×25 ml). The combined ethyl acetate fractions were washed with water (2×20 ml), brine (20 ml), dried over MgSO$_4$ and evaporated to give the title compound (266 mg) as a white solid.
TLC $R_f$ 0.10 (ethyl acetate)
MS 372 (M$^+$)

Similarly prepared were:

EXAMPLE 15

4-((3-(4-Phenylphenoxy)propylsulfonyl)methyl)
-tetrahydropyran-4-carboxylic Acid From Example 9 (300 mg) as a white solid (203 mg).
TLC $R_f$ 0.15 (ethyl acetate)
MS 418(M$^+$)

EXAMPLE 16

4-((3(3Pyridyloxy)propylsufonyl)methyl)
tetrahydropyran-4-carbonxylate

From Example 10 (325 mg) as a white solid (103 mg).
TLC $R_f$ 0.10(ethyl acetate)
MS 343 (M$^+$)

EXAMPLE 17

1-{2-[1-(4-Nitrophenyl)pyrrolidin-3-yl]
ethanesulfonylmethyl}-cyclobutanecarboxylic acid Prepared in the same manner as Example 14 from Example 11 (60 mg) and lithium hydroxide monohydrate (29 mg) to give Example 17 (75 mg) as a yellow solid.

TLC $R_f$ 0.44 (5% methanol in dichloromethane)
MS 397 (MH$^+$)

EXAMPLE 18

2-(3-Phenoxypropane-1-sulfonyl)
cyclopentanecarboxylic acid

Prepared in the same manner as Example 14 from Example 12 (163 mg) and lithium hydroxide (105 mg) to give the title compound (134 mg) as a white solid.
TLC $R_f$ 0.34 (1:1 hexane-ethyl acetate+1% acetic acid)
MS 311 (M–H)

EXAMPLE 19

4-(1-Methoxycarbonylcyclohexylmethylsulfanyl)
piperidine-1-carboxylic acid tert-butyl ester Intermediate 6 (0.50 g) and Intermediate 12 (0.46 g) were combined in anhydrous methanol, degassed, cooled to −10° C., and treated with sodium bis(trimethylsilyl)amide (1.78 ml, as a 1.0 M solution in tetrahydrofuran), and the mixture stirred for 18 h, slowly warming to room temperature. The reaction was then reduced in vacuo, diluted with water (20 ml) and extracted with ethyl acetate (2×20 ml). The combined organic extracts were washed with aqueous 2% citric acid (20 ml), water (20 ml), saturated sodium bicarbonate (20 ml), saturated brine (20 ml), dried (Na$_2$SO$_4$) and solvents removed in vacuo to leave a straw coloured oil. This crude product was the purified by silica gel column chromatography, eluting with a gradient of 2% diethyl ether in dichloromethane rising to 4% diethyl ether in dichloromethane, to furnish the title compound as a colourless oil (0.29 g, 44%).
TLC $R_f$ 0.31 (4% diethyl ether/dichloromethane)
MS: 372 (MH$^+$)

EXAMPLE 20

2-(Piperidin-4-ylsulfanyl)cyclopentanecarboxylic
acid methyl ester

Methyl 1-cyclopentene-1-carboxylate (0.24 ml) and Intermediate 12 (0.50 g) were dissolved in anhydrous methanol (20 ml), degassed with nitrogen, and cooled to −10 to −15° C. Sodium bis(trimethylsilyl)amide, 1.0 M in tetrahydrofuran (1.93 ml) was added and the reaction stirred for 18 h, warming to room temperature. The reaction mixture was then evaporated and the residue partitioned between ethyl acetate (20 ml) and water (20 ml). The aqueous was extracted once more with ethyl acetate (10 ml) and the combined organic extracts were washed with 2% aqueous citric acid (20 ml), water (20 ml), saturated sodium bicarbonate (20 ml), saturated brine (20 ml), dried (Na$_2$SO$_4$) and evaporated under reduced pressure.

The resultant amber oil was dissolved in dichloromethane (10 ml) and treated with trifluoroacetic acid (2 ml). After stirring at room temperature for 17 h, the solvents were evaporated and the residue azeotroped with 1:1 dichloromethane/hexane (3×20 ml). The residue was then dissolved in water (30 ml) and washed with diethyl ether (2×10 ml) before being basified with sodium carbonate to pH 11 and extracted with ethyl acetate (4×15 ml). The combined ethyl acetate extracts were then washed with saturated brine (10 ml), dried (Na$_2$SO$_4$) and reduced in vacuo to provide the title compound as a colourless gum (0.15 g, 31%).

TLC R$_f$0.26 (6% methanol/dichloromethane containing a trace of aqueous ammonia)
MS 244 (MH$^+$)

EXAMPLE 21

1-(Piperidin-4-ylsulfanylmethyl) cyclohexanecarboxylic acid methyl ester

Example 19 (0.28 g) was dissolved in dichloromethane (10 ml) and treated with trifluoroacetic acid (2 ml). The solution was stirred at room temperature for 5 h, then evaporated under reduced pressure, and the residue azeotroped with 1:1 dichloromethane/hexane (2×20 ml). The resultant gum was then dissolved in water (30 ml) and washed with diethyl ether (2×10 ml), back-extracting the organic washes with aqueous 1% citric acid (2×5 ml). The aqueous phase was then basified with potassium carbonate to pH 11/12, saturated with solid sodium chloride, and extracted with ethyl acetate (4×10 ml). The combined organic extracts were washed with saturated brine (10 ml), dried (Na$_2$SO$_4$) and reduced under vacuum to give the title compound as a colourless gum (0.19 g, 92%).
TLC R$_f$0.25 (6% methanol/dichloromethane containing a trace of aqueous ammonia)
MS: 272 (MH$^+$)

EXAMPLE 22

2-[1-(4-Cyanophenyl)piperidin-4-ylsulfanyl] cyclopentane -carboxylic acid methyl ester Example 20 (0.143 g), 4-fluorobenzonitrile (0.142 g) and potassium carbonate (0.081 g) were combined in anhydrous N,N-dimethylformamide (10 ml) and heated to 100° C. for 3 h, under nitrogen. After cooling, the reaction mixture was poured onto water (100 ml) and extracted with ethyl acetate (2×30 ml). The organic extracts were then washed with water (2×20 ml), aqueous 1% citric acid (30 ml), water (10 ml), saturated sodium bicarbonate (20 ml), saturated brine (20 ml), dried (Na$_2$SO$_4$) and evaporated to dryness. The residue was purified by silica gel column chromatography with 1:1 hexane/diethyl ether as eluent to furnish the title compound as a colourless gum (0.036 g,
TLC R$_f$0.44 (1:1 hexane/diethyl ether)
MS: 345 (MH$^+$)

The following compounds were prepared in a similar manner:

EXAMPLE 23

1-[1-(4-Nitrophenyl)piperidin-4-ylsulfanylmethyl] cyclo -hexanecarboxylic acid methyl ester Prepared in the same manner as Example 22 from Example 21 (0.19 g) and 1-fluoro-4-nitrobenzene (0.20 g), with 1-methyl-2-pyrrolidinone (10 ml) as solvent, to yield the title compound as a yellow gum (0.25 g, 91%).
TLC R$_f$0.33 (3:2 hexane/diethyl ether)
MS 393 (MH$^+$)

EXAMPLE 24

2-[1-(4-Cyanophenyl)piperidin-4-ylsulfanyl] cyclopentane -carboxylic acid

Lithium hydroxide monohydrate (0.022 g), as a solution in water (3 ml), was added dropwi/se to a stirred solution of Example 22 (0.036 g) in dioxane, held at just above its freezing point in an ice/sodium chloride bath. The mixture was then stirred in the ice bath, slowly warming to room temperature over 3 h. The reaction mixture was then reduced under vacuum, and the residue diluted with water (10 ml) and washed with diethyl ether (2×10 ml), back-extracting the ether washes with dilute sodium bicarbonate solution (2×5 ml). The aqueous phase was then acidified with citric acid to pH 4/5 and extracted with ethyl acetate (3×10 ml). The combined ethyl acetate extracts were washed with water (2×10 ml), saturated brine (10 ml), dried.(Na$_2$SO$_4$) and reduced in vacuo to give the title compound as a colourless gum (0.035 g, 100%)
TLC R$_f$0.39 (1:1 ethyl acetate/hexane)
MS 331 (MH$^+$)

EXAMPLE 25

1-[1-(4-Nitrophenyl)piperidin-4-ylsulfanylmethyl] cyclohexane -carboxylic acid

Example 23 (0.24 g) and lithium hydroxide monohydrate (0.13 g) were combined in tetrahydrofuran (10 ml), methanol (5 ml) and water (2.5 ml) and heated to reflux for 7 h. The reaction was then cooled and reduced under vacuum. The residue was diluted with water (40 ml) and washed with ethyl acetate (2×20 ml), back-extracting with dilute sodium bicarbonate (2×10 ml). The combined aqueous phase was then acidified with citric acid to pH 4 and extracted with ethyl acetate (2×20 ml). The combined ethyl acetate extracts were washed with water (2×10 ml), saturated brine (20 ml), dried (Na$_2$SO$_4$) and reduced under vacuum to provide the title compound as a yellow solid (0.083 g, 35%).
TLC R$_f$0.45 (1:1 hexane/ethyl acetate)
MS 379 (MH$^+$)

EXAMPLE 26

1-[1-(4-Nitrophenyl)piperidine-4-sulfinylmethyl] cyclohexane -carboxylic acid

Oxone (0.133 g) was dissolved in water (10 ml) and added to a solution of Example 25 (0.083 g) in methanol (10 ml), cooled in an ice/salt bath. The resultant suspension was vigorously stirred for 3 days, warming to room temperature. The reaction mixture was then diluted with water (35 ml) and extracted with dichloromethane (3×15 ml). The combined organic extracts were washed with water (10 ml), saturated brine (10 ml), dried (Na$_2$SO$_4$) and reduced in vacuo to leave a yellow solid which was triturated with several small portions of dichloromethane to provide the title compound as a yellow solid (0.049 g, 56%)
TLC R$_f$0.30 (5% methanol/dichloromethane)
MS 379 (MH$^+$)

EXAMPLE 27

4-((3-(4-Chlorophenoxy)propylsulfonyl)methyl) tetrahydro -pyran-4-carboxylic acid N-hydroxy amide EDC (40 mg) was added to a solution of Example 13 (75 mg) in dichloromethane (20 ml), followed by tert-butyldimethylsilylhydroxylamine (32 mg) and N,N-dimethylaminopyridine (2 mg), and the resulting clear solution was stirred at room temperature for 3 h. The mixture was then washed with water, saturated bicarbonate and brine, dried over MgSO$_4$ and evaporated. The residue was dissolved in a minimum amount of fresh dichloromethane and 1M aqueous hydrochloric acid in ether (2 ml) was added. The solution was stirred for 10 min, then evaporated and the residue purified by chromatography on silica, eluting with ethyl acetate, to give the title compound (30 mg) as a colourless glass.
TLC R$_f$ 0.27 (EtOAc)
MS 391 (M$^+$)

EXAMPLE 28

4-((3-(4-Methoxyphenoxy)propylsulfonyl)methyl)-tetrahydropyran-4-carboxylic acid N-hydroxy amide To a stirred solution of Example 14 (250 mg) in dichloromethane (15 ml) containing a drop of DMF was added oxalyl chloride (256 mg). The mixture was stirred for 1 h before removing the solvent under reduced pressure. The residue was treated three times with a mixture of dichloromethane/hexane (1:1; 50 ml) and evaporated to dryness. The residue was dissolved in THF (15 ml) and treated with an aqoueus solution of hydroxylamine (50 wt %; 0.21 ml). The mixture was stirred for 1 h before diluting with water (10 ml) and extracting with ethyl acetate (3×10 ml). The combined ethyl acetate extracts were washed with saturated sodium bicarbonate solution (20 ml), water (20 ml), brine (20 ml), dried over MgSO$_4$ and evaporated to yield the title compound (145 mg) as a colourless solid.
TLC R$_f$ 0.60 (9:1 dichloromethane/methanol)
MS 387 (M$^+$)
Similarly prepared was:

EXAMPLE 29

4-((3-(4-Phenylphenoxy)propylsulfonyl)methyl)-tetrahydropyran-4-carboxylic Acid N-hydroxy amide From Example 15 (180 mg) as a white solid (124 mg).
TLC R$_f$ 0.42 (9:1 dichloromethane/methanol)
MS 433 (M$^+$)

EXAMPLE 30

1-{2-[1-(4-Nitrophenyl)pyrrolidin-3-yl]-ethanesulfonylmethyl}-cyclobutanecarboxylic acid hydroxyamide Prepared in the same manner as Example 28 from Example 17 (75 mg), oxalyl chloride (0.06 ml) and hydroxylamine (50% in water, 0.06 ml) to give Example 31 (66 mg) as a yellow solid.
TLC R$_f$ 0.35 (5% methanol in dichloromethane)
MS412 (MH$^+$)

EXAMPLE 31

2-(3-Phenoxypropane-1-sulfonyl) cyclopentanecarboxylic acid hydroxyamide

Prepared in the same manner as Example 28 from Example 18 (121 mg), oxalyl chloride (0.135 ml) and hydroxylamine (50% in water, 0.12 ml) to give the title compound (84 mg) as a white solid.
TLC R$_f$ 0.29 (5% methanol in dichloromethane)
MS328(MH$^+$)

What is claimed is:
1. A compound of formula (I)

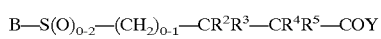  (I)

wherein
Y is selected from the group consisting of OR$^1$ and NHOH;
R$^2$ is independently selected from the group consisting of H and a moiety (optionally substituted with R$^{10}$) selected from C$_{1-6}$ alkyl, C$_{2-6}$ alkenyl, aryl, C$_{1-6}$ alkyl-aryl, cycloalkyl and C$_{1-6}$ alkyl-cycloalkyl;
R$^1$ and R$^3$ are independently selected from the group consisting of H and C$_{1-6}$ alkyl; or
CR$^2$R$^3$ is a cycloalkyl ring optionally substituted with R$^{10}$ or a group (optionally substituted with R$^{10}$) selected from C$_{1-6}$ alkyl, aryl, and C$_{1-6}$ alkyl-aryl;
CR$^4$R$^5$ is tetrahydropyran optionally substituted with R$^{10}$;
B is selected from the group consisting of C$_{1-8}$ alkyl, C$_{2-6}$ alkenyl and C$_{2-6}$ alkynyl, and is substituted with R$^6$;
R$^6$ is selected from the group consisting of N(R$^7$)$_2$, OR$^7$, COR$^7$, C(=NOR$^9$)R$^7$, NR$^7$R$^8$, S(O)$_{0-2}$R$^9$, and SO$_2$N(R$^7$)$_2$;
R$^7$ is selected from the group consisting of H and a moiety selected from C$_{1-6}$ alkyl, aryl, C$_{1-6}$ alkyl-aryl, cycloalkyl, and C$_{1-6}$ alkyl-cycloalkyl, wherein said moiety is optionally substituted with R$^9$, COR$^9$, SO$_{0-2}$R$^9$, CO$_2$R$^9$, OR$^9$, CONR$^1$R$^9$, NR$^1$R$^9$, halogen, CN, SO$_2$NR$^1$R$^9$ or NO$_2$, and for each case of N(R$^7$)$_2$ the R$^7$ groups are the same or different;
R$^8$ is selected from the group consisting of COR$^7$, CON(R$^7$)$_2$, CO$_2$R$^9$ and SO$_2$R$^9$;
R$^9$ is selected from the group consisting of C$_{1-6}$ alkyl, aryl, and C$_{1-6}$ alkyl-aryl; and
R$^{10}$ is selected from the group consisting of OR$^7$, COR$^7$, CO$_2$R$^1$, CON(R$^7$)$_2$, NR$^7$R$^8$, S(O)$_{0-2}$R$^9$, SO$_2$N(R$^7$)$_2$, CN, and halogen; or a salt, solvate, hydrate, N-oxide or protected amino, protected carboxy or protected hydroxamic acid derivative thereof.

2. The compound of claim 1, wherein R$^2$ is optionally substituted C$_{1-6}$ alkyl or CR$^2$R$^3$ forms the said optionally substituted ring.

3. The compound of claim 1, wherein B is C$_{1-8}$ alkyl substituted with R$^6$.

4. The compound of claim 3, wherein B is C$_{1-8}$ alkyl substituted with OR$^7$.

5. The compound of claim 4, wherein R$^7$ is optionally substituted aryl.

6. The compound of claim 1, wherein S(O)$_{0-2}$ is SO$_2$.

7. The compound of claim 1, selected from the group consisting of
4-((3-(4-chlorophenoxy)propylsulfanyl)methyl)-tetrahydropyran4-carboxylic acid and
4-((3-(4-chlorophenoxy)propylsulfonyl)methyl)-tetrahydropyran-4-carboxylic acid or its N-hydroxy amide.

8. A compound selected from the group consisting of
methyl 4-(3-hydroxypropylsulfanylmethyl) tetrahydropyran-4-carboxylate,
methyl 4-((3-(4-methoxyphenoxy)propylsulfanyl) methyl)tetrahydropyran-4-carboxylate,
methyl 4-((3-(4-phenylphenoxy)propylsulfanyl)methyl) tetrahydropyran-4-carboxylate,
methyl 4-((3-(4-methoxyphenoxy)propylsulfonyl) methyl)tetrahydropyran-4-carboxylate,
methyl 4-((3-(4-phenylphenoxy)propylsulfonyl)methyl) tetrahydropyran-4-carboxylate,
4-((3-(4-methoxyphenoxy)propylsulfonyl)methyl) tetrahydropyran-4-carboxylic acid, 4-((3-(4-phenylphenoxy)propylsulfonyl)methyl) tetrahydropyran-4-carboxylic acid, 4-((3-(4-methoxyphenoxy)propylsulfonyl)methyl) tetrahydropyran-4-carboxylic acid N-hydroxy amide, and 4-((3-(4-phenylphenoxy)propylsulfonyl)methyl) tetrahydropyran-4-carboxylic acid N-hydroxy amide.

9. A pharmaceutical composition for use in therapy, comprising a compound of claim 1, and a pharmaceutically-acceptable diluent or carrier.

10. A method for the treatment of rheumatoid arthritis, which comprises administering to a subject in need thereof an effective amount of a compound of claim 1.

\* \* \* \* \*